United States Patent [19]
Oladele et al.

[11] Patent Number: 6,037,332
[45] Date of Patent: Mar. 14, 2000

[54] METHOD OF URINARY BLADDER INSTILLATION

[75] Inventors: Alawode Oladele, Tucker; Sam D. Graham, Atlanta; John A. Petros, Norcross, all of Ga.

[73] Assignee: Emory University, Atlanta, Ga.

[21] Appl. No.: 08/803,310

[22] Filed: Feb. 20, 1997

Related U.S. Application Data

[60] Provisional application No. 60/011,945, Feb. 20, 1996.

[51] Int. Cl.$^7$ .......................... A61K 31/715; A01N 41/02
[52] U.S. Cl. .................................. 514/59; 514/1; 514/25; 514/23; 424/422
[58] Field of Search .............................. 514/59, 25, 577, 514/1, 23; 424/422, 434

[56] References Cited

U.S. PATENT DOCUMENTS 5,055,301  10/1991  Voight .
5,453,444   9/1995  Strassman .

FOREIGN PATENT DOCUMENTS 9300051  1/1993  WIPO .

OTHER PUBLICATIONS

Whiteley, Toxicologic Pathology 24:681 1996.
Newman, Urology Times, Aug. 1995, p. 15.
Shintani Clin. Exp. Immunol 108:1997.
Imagawa, Gankagakuryoho Jul. 1 (127–131)1980 (Abstract Only).
Oladele J. Urology 153:233A Apr. 1995.
Oladele Proc. Ann. Meet Am. Assoc. Cancer Res., 26:A3590 Mar. 1995.
Kellner, Verh. Dtsch. Ges. Pathol 77:124, 1993 (abstract only).
Coffey, R.J. Jr. et al., "Suramin Inhibition of Growth Factor Receptor Binding and Mitogenicity in AKR–2B Cells," (1987) *J. Cellular Physiology* 132:143–148.
Gansler, T. et al., "Suramin Inhibits Growth Factor Binding and Proliferation by Urothelial Carcinoma Cell Cultures," (1992) *J. Urology* 148:910–914.
Graham, S.D. Jr. et al., "Intravesical Suramin in the Prevention of Transitional Cell Carcinoma," (1995) *Urology* 45(1):59–63.
Pollak, Michael and Richard, Martine, "Suramin Blockade of Insulinlike Growth Factor I–Stimulated Proliferation of Human Osteosarcoma Cells," (1990) *J. National Cancer Institute* 82(16):1349–1352.
Smith, K. et al., "Characterization and Quantitation of the Epidermal Growth Factor Receptor in Invasive and Superficial Bladder Tumors," (1989) *Cancer Reserach* 49:5810–5815.
Sorimachi, K. et al., "Inhibition of Fibroblast Growth by Polyanions; Effects of Dextran Sulfate and Lignin Derivatives," (1992) *Cell Biology International Reports* 16(1)63–71.

*Primary Examiner*—Nancy A. Johnson
*Attorney, Agent, or Firm*—Greenlee Winner and Sullivan PC

[57] ABSTRACT

Growth of transition cell carcinoma cells is found to be inhibited by dextran sulfate. Intravesicular instillation of a dextran sulfate solution prevents growth of bladder carcinoma cells. Dextran sulfate has an inhibitory effect on binding of insulin-like growth factor to bladder tumor cells.

8 Claims, 2 Drawing Sheets

BLADDER HISTOLOGY
MNU GROUP (18 ANIMALS)

| HISTOLOGY | NUMBER OF CASES |
|---|---|
| Cancer | 10 |
| Proliferation | 6 |
| Stones | 2 |
| Normal | 0 |

2 Animals died

FIG. 3

BLADDER HISTOLOGY
DEXTRAN SULFATE/MNU GROUP (20 ANIMALS)

| HISTOLOGY | NUMBER OF CASES |
|---|---|
| Cancer | 2 |
| Proliferation | 11 |
| Cystitis | 1 |
| Normal | 6 |

FIG. 4

METHOD OF URINARY BLADDER INSTILLATION

CROSS REFERENCE TO RELATED APPLICATIONS

Priority is claimed from U.S. Provisional Application No. 60/011,945 filed Feb. 20, 1996.

STATEMENT RE. FEDERALLY SPONSORED RESEARCH AND DEVELOPMENT

Not applicable

BACKGROUND OF THE INVENTION

Ninety percent (90%) of bladder cancers are transitional cell carcinomas which are superficial at early stage but later become invasive. Surgical removal is possible but a high rate of recurrence is experienced. Surgical removal is therefore often followed by further treatment, either to prevent recurrence or to inhibit the growth of tumor cells that were not surgically removed. Various agents are employed, administered by instillation into the bladder (intravesicular instillation). Adverse reactions and toxic effects often limit the duration of treatment and prevent commencement of treatment until several weeks after surgery.

Reports on the use of dextran sulfate as an inhibitor of tumor cell growth are rare. U.S. Pat. No. 5,055,301 to Voigt et al discloses inhibition of both androgen-dependent and androgen independent prostate carcinoma cells in culture. In vivo data were not reported. Imagawa, A. et al., (1980) Gan Kagakuryoho 7:127–131, reported that a combination of carboquone, cytarabine and dextran sulphate instilled into the bladder of post-operative bladder cancer patients yielded no recurrences in 21 patients. Previous studies have shown that polyanionic drugs such as Suramin also inhibit binding of growth factors to their receptors and inhibit cell proliferation [Gansler, T. et al. (1992) *J. Urol.* 148:910; Pollack, M. et al. (1990) *J. Natl. Cancer Inst.* 82: 1349; Coffey, R. J. Jr., et al. (1987) 132: 143–148]. On the other hand, Sorimachi, K. et al., (1992) Cell Biol. Int. Rep. 16: 63–72, failed to observe an inhibitory effect of dextran sulfate or other polyanionic compounds on the growth of human urinary bladder carcinoma cells in culture. It has been shown that the in vitro inhibition of T24 and HT1376 transitional cell carcinoma cell line proliferation by Suramin results from specific inhibition of epidermal growth factor (EGF) and insulin-like growth factor 1 (IGF-1) binding (Gansler, supra). The in-vivo action of Suramin was demonstrated by documenting intravesical inhibition of MNU induced bladder tumors in Fisher 344 rats [Graham, S. D. Jr., et al. (1995) *J. Urology* 45(1): 59–63]. Dextran sulfate is also a polyanionic compound which, like Suramin, has minimal toxicity and can safely be administered intravenously [Smith K. et al. (1989) *Cancer Res.* 49(21): 5810–5815].

SUMMARY OF THE INVENTION

The invention relates to the observation that dextran sulfate inhibits the growth of transitional cell carcinoma cells in vitro and inhibits the formation of bladder carcinoma tumors in rats. These observations have lead to a method of treating human patients to prevent development of transitional cell carcinomas of the urinary bladder. The method includes instillation of an effective amount of dextran sulphate into the bladder at intervals and for a period encompassing several such treatments. The method has several advantages in that there are no known toxic effects at the effective doses, nor inflammatory effects. Treatment can be commenced immediately post-operatively, and need not be discontinued for failure of the patient to tolerate the treatment. Furthermore, the treatment can be used in situations where current methods have had to be discontinued. Efficacy of treatment can be monitored by cystoscopy and the optimum dose regimen can be modified as needed.

DESCRIPTION OF THE DRAWINGS

FIG. 3 is a summary of the histological results of the animals treated with MNU only, as described in Example 2.

FIG. 4 is a summary of the histological results of the animals treated with MNU and dextran sulfate, as described in Example 2.

DETAILED DESCRIPTION OF THE INVENTION

Figure 1:
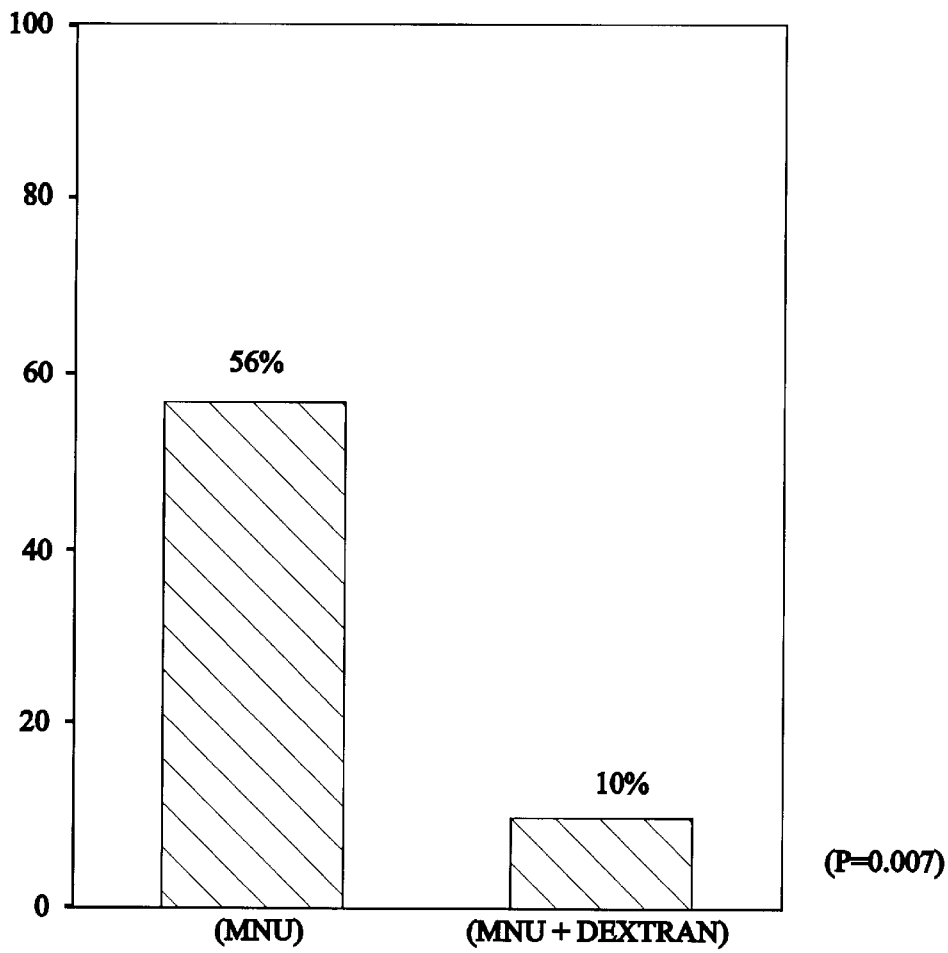
FIG. 1 is a bar graph of tumor incidence in rats treated with a carcinogen (MNU) with or without treatment with dextran sulfate as described in Example 2.
Figure 2:
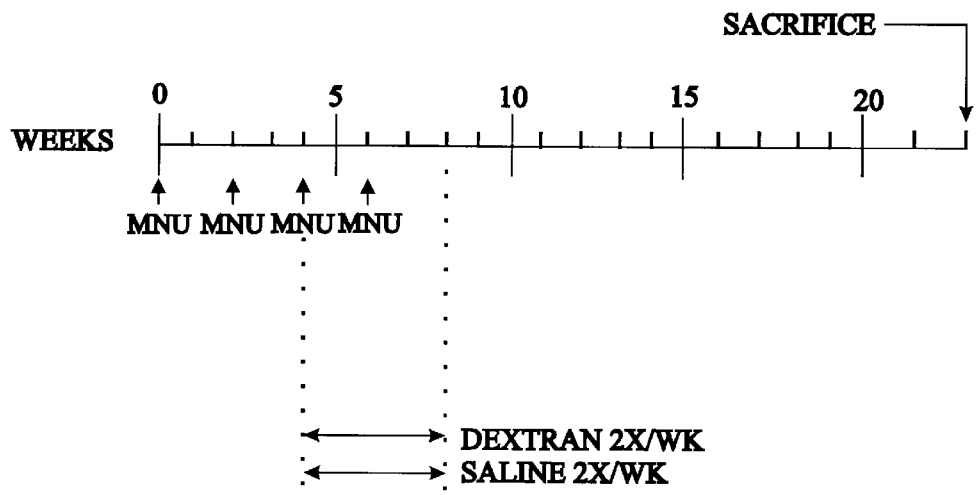
FIG. 2 is a diagrammatic representation of the time of administration of the MNU and dextran sulfate in the protocol of Example 2.

Optimum effective dose of dextran sulfate is 200–4000 mg/dose. Dextran sulfate having an average molecular weight of about 8000 daltons is preferred. Instillation is carried out by known methods. Dextran sulfate is dissolved in a physiologically acceptable aqueous solvent. The dose to be administered is dissolved in a suitable volume (e.g. 200 ml), intended to be retained in the bladder for about one hour. The dextran sulfate is instilled via a catheter into the bladder. A typical treatment regimen is once weekly for eight weeks. However both the frequency and duration of treatments can be modified in the light of clinical experience.

The invention also includes a kit for carrying out the method conveniently. Such a kit includes pre-weighed dextran sulfate and pre-measured solvent, each in unit dosage form, together with a suitable catheter and means, such as a syringe or pump, for causing the dextran sulfate solution to enter the bladder via the catheter. Although the unit dosage of dextran sulfate can, in principle, be provided in solution, it is preferred to provide the dextran sulfate in dry powder form, since shelf life is likely to be greater and the kit can then be stored at room temperature. Convenient packaging can be provided such that the solvent can be added directly to the dry dextran sulfate without exposure to the atmosphere, thereby preserving sterility. Such packaging can include, for example, a container divided into separate compartments, one for solvent and one for dextran sulfate. Prior to use, a barrier separating the two compartments can be removed or penetrated, allowing the dextran sulfate to be dissolved. The container can then be connected directly to the syringe so that the solution need never be exposed to the ambient air prior to administration.

In its simplest form the invention is therefore a method of instillation into the bladder of a patient that includes introducing into the bladder a solution of dextran sulfate in a volume retainable by the patient for about an hour, and repeating the step of introducing dextran sulfate periodically at intervals for a desired number of times.

The experiments supporting the invention are described in the following examples.

EXAMPLE 1

Dextran Sulfate Inhibits the Proliferation of Human Transitional Cell Carcinoma Cultures Method: Cultures of two urothelial carcinoma cell lines, HT 1376 and T24 were obtained from the American Type Culture Collection and propagated in Dulbecco's Modified Eagles Medium (DMEM) supplemented with 10% fetal bovine serum (FBS). The HT1376 and T24 cells were plated into 96 well polystyrene trays in 0.1 ml of medium at densities of 5000 and 2500 cells/wells respectively. After overnight incubation, medium was replaced with DMEM containing various FBS and dextran sulfate concentrations. Each FBS and dextran sulfate concentration was tested in quadruplicated wells. On day eight the cells were fixed with glutaraldehyde, stained with 0.1% crystal violet and absorbance at 540 nm was quantitated in a (Bio-Rad) microplate spectrophotometer.

Results: The ratio of A540 values in day one and day eight was used to indicate cell proliferation. T24 cell proliferation was completely inhibited (p<0.0001) by 10 mM dextran sulfate with half maximal effect at approximately 1 mM.

Conclusion: Dextran sulfate is a potent cytostatic agent for human urothelial cells in vitro.

The in vitro proliferation data are consistent with our in vivo results. All indications are that this agent may be highly effective as an intravesical agent for treatment of transitional cell carcinoma.

EXAMPLE 2

Intravesical Dextran Sulfate for Chemoprevention of Transitional Cell Carcinoma of the Bladder For this study, we used a N-methyl-N-nitrosurea (MNU)-induced rat bladder transitional cell carcinoma in vivo model introduced by Hicks, et al. (1972) and modified by Steinberg, et al. (1990).

Animals: Four to five week old female Fisher 344 rats (avg. Wt. 200 g) were used in all cohorts on this trial. All animals received 5 mg/200 g body weight intraperitoneal gentamicin (50 mg/ml) as antibacterial prophylaxis one hour prior to each bladder catheterization.

MNU dose and schedule: 100 mg of MNU (Sigma, St. Louis, Mo.) were dissolved in 10 ml of sodium acetate ($CH_3COONa$), pH of a solution=6.5. Five mg/200 g body weight of this solution (0.5 ml) was instilled intravesically via a 22-gauge teflon angiocatheter under a continuous flow hood within 45 minutes of preparing the MNU solution every other week for a total of 4 doses (8 weeks).

Dextran Sulfate: (Mol. Wt. 8000 Da.-Sigma, St. Louis, Mo.) Beginning at week four, 20 of the animals received intravesical dextran sulfate, 10 mg/200 g body weight twice a week for four weeks. The remaining 20 animals received saline on the same schedule.

Tissue Preparations: The urinary bladder were excised, filled and fixed with 10% neutral buffered formalin, and then embedded in paraffin. The bladders were sectioned every 2 mm and 5-micron sections were stained with hematoxylin and eosin.

Conclusion: Intravesical dextran sulfate effectively prevents the development of transitional cell carcinoma of the bladder. Intravesical instillation of dextran sulfate did not cause any significant side effects or histopathologic changes in urinary bladders of female Fisher 344 rats.

EXAMPLE 3

The Inhibition of Growth Factor Binding by a Polyanionic Compound (Dextran Sulfate) in Urothelial Tumors Method: Growth factor receptor binding studies were performed using T24 high grade human bladder tumor cell line. Cells were incubated with 10 $\mu$M $^{125}$I-Insulin like growth factor-1 ($^{125}$I-IGF-1) or $^{125}$I-epidermal growth factor ($^{125}$I-EGF) and varying concentration of unlabeled growth factor or dextran sulfate in 1 ml of binding assay buffer. After incubation at 4° C. for 10 to 12 hours, the assay buffer was removed and the cultures washed three times. The cells and receptor-bound growth factors were then solubilized in 1 ml of 0.5 NaOH before being quantitated in a gamma radiation counter.

Results: Maximal inhibition of $^{125}$I-IGF-1 binding (35% of control binding) to T24 cells was produced by dextran sulfate concentration of 10 mM. Dextran sulfate had a biphasic effect on EGF binding with a modest inhibition at (80% of control binding) 1–2 mM and increased binding (115% of control) at 10 mM.

Conclusion: Our in vitro studies have demonstrated that dextran sulfate inhibits proliferation of the human urothelial carcinoma cell line T24, and specifically inhibits binding of IGF-1 and EGF to these cells. Dextran sulfate had a more pronounced inhibitory effect on IGF-1 binding than on EGF binding which is a similar effect of other polyanionic compounds such as suramin. Unlike other polyanionic compounds and other intravesical agents used in treating bladder cancer, dextran sulfate has no known significant toxicity.

We claim:

1. A method for inhibiting growth of transition cell carcinoma cells comprising administering by intravesicular instillation a growth inhibitory amount of dextran sulfate free of carboquone and cytarabine to said cells.

2. The method of claim 1 wherein the step of administering comprises intravesicular instillation of dextran sulfate in a physiologically acceptable aqueous solvent at a dose of 200–4000 mg dextran sulfate per dose.

3. The method of claim 2 wherein the dextran sulfate is administered in a volume retainable for about one hour.

4. The method of claim 2 wherein the amount of dextran sulfate is sufficient to inhibit binding of IGF-1 to said cells.

5. The method of claim 1 wherein the dextran sulfate has an average molecular weight of about 8000 daltons.

6. A method of inhibiting binding of IGF-1 to human bladder tumor cells comprising contacting the cells by intravesicular instillation of a solution of dextran sulfate free of carboquone and cytarabine in a physiologically acceptable aqueous solvent, in an IGF-1 inhibiting concentration.

7. The method of claim 6 wherein the concentration of dextran sulfate is 10 mM.

8. A kit for intravesicular instillation of dextran sulfate comprising pre-weighed dextran sulfate free of carboquone and cytarabine in unit dosage form, a pre-measured, physiologically acceptable aqueous solvent in unit dosage volume and means for intravesicular instillation of a solution of dextran sulfate.

* * * * *